United States Patent [19]

Buschhoff et al.

[11] 3,994,944

[45] Nov. 30, 1976

[54] METHOD FOR MAKING ALKYL TIN TRICHLORIDES

[75] Inventors: Max Buschhoff, Luenen; Karl Heinz Müeller, Werne, both of Germany

[73] Assignee: Schering Aktiengesellschaft, Bergkamen, Germany

[22] Filed: Sept. 12, 1975

[21] Appl. No.: 612,956

[30] Foreign Application Priority Data

Sept. 19, 1974 Germany.............................. 2447786

[52] U.S. Cl. ............................................ 260/429.7
[51] Int. Cl.² ............................................ C07F 7/22
[58] Field of Search ................................. 260/429.7

[56] References Cited
UNITED STATES PATENTS

| | | | |
|---|---|---|---|
| 3,061,647 | 10/1962 | Jenkner ....................... | 260/429.7 X |
| 3,287,386 | 11/1966 | Neumann ........................ | 260/429.7 |
| 3,454,569 | 7/1969 | Glaskey ............................ | 260/429.7 |
| 3,754,012 | 8/1973 | Bulten.............................. | 260/429.7 |
| 3,894,066 | 7/1975 | Buschhoff........................ | 260/429.7 |

OTHER PUBLICATIONS

Chemical Abstracts, V60, 3008a (1964).

Chemical Abstracts, V59, 12842 (1963).

*Primary Examiner*—Helen M. S. Sneed
*Attorney, Agent, or Firm*—Donald R. Bentz

[57] ABSTRACT

A method for the monoalkylation of tin tetrachloride by reaction of tin tetrachloride at 20° –70° C. with a stoichiometric amount of an ether donor complex or of a tertiary amine donor complex of an aluminum trialkyl or alkyl aluminum halide.

8 Claims, No Drawings

METHOD FOR MAKING ALKYL TIN TRICHLORIDES

The present invention relates to methods for making alkyl tin trichlorides, and relates in particular to methods for the monoalkylation of tin tetrachloride.

Alkyl tin trichlorides are important precursors for the preparation of stabilizers for polyvinyl chloride. The introduction of alkyl groups onto the tin atom can take place in different ways (cf. W. P. Neumann, Die organische Chemie des Zinns, Ferdinand Enke Verlag, Stuttgart, 1967, pages 16 – 35). Nevertheless, in most cases a mixture of higher alkylated tin chlorides is obtained. This is particularly true for the preparation of alkyl tin chlorides from tin tetrachloride and alkyl aluminum compounds. In this case, a mixture of trialkyl tin chloride and tetraalkyl tin is produced. The lower alkylation stages are then attainable by so-called comproportionation (loc. cit., pages 41 – 43). Alkyl tin trichloride is obtained, for example, by comproportionation of tetraalkyl tin with tin tetrachloride:

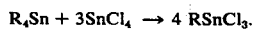
$R_4Sn + 3SnCl_4 \rightarrow 4 RSnCl_3.$

The preparation of alkyl tin trihalides according to this process is, however, limited to a few alkyl groups (for example the vinyl group) and occurs only in a special solvent ($POCl_3/P_2O_5$). The reason for this difficulty is that the step necessary for complete comproportionation,

$R_2SnCl_2 + SnCl_4 \rightarrow 2 RSnCl_3,$ can be realized only in exceptional cases. Nevertheless, methods have been developed according to which alkyl tin trichloride is formed in addition to dialkyl tin- or trialkyl tin chlorides (cf. German Pat. No. 1,161,893 or British Pat. No. 739,883).

Alkyl tin trichloride can be obtained from such mixtures, for example by distillation. However, this method is strongly limited because of the high boiling point of long chain alkyl tin trichlorides and can be technically carried out for the preparation of short chain ( $\leq C_4$) alkyl tin trichlorides only.

The simplest possibility for preparing alkyl tin trichlorides would be by the replacement of a chlorine atom from $SnCl_4$ by an alkyl group, i.e. by a direct monoalkylation. A monoalkylation of $SnCl_4$ has heretofore not been successfully carried out with the technically available aluminum trialkyls. However, alkyl tin trichlorides can be prepared from $SnCl_4$ by monoalkylation with alkyl aluminum alkoxides [cf. German Offenlegungsschrift Pat. No. 2,304,617 and W. P. Neumann Ann. Chem. 653, 163 (1962)]. But in this process the great economic advantage which the aluminum trialkyls possess in alkylation reactions, in comparison with other akylating agents, is limited. Namely, ith alkyl aluminum akoxides, a maximum of only two alkyl groups can be transferred per aluminum atom.

According to German Auslegeschrift 1,157,617 and 1,164,407, it is possible, by the use of alkyl aluminum ether complexes or alkyl aluminum amine complexes, to prepare trialkyl tin compounds and dialkyl tin compounds, or mixtures of the same, according to a stoichiometric or non-stoichiometric reaction. The preparation of mono-alkyl tin compounds by this method has heretofore not been possible.

In a later publication, Liebigs Ann. Chem. 653, 160 (1962), W. P. Neumann writes:

"It was now to be investigated whether the reaction of aluminum alkyls with tin tetrachloride could be so directed that one could, according to the reactions

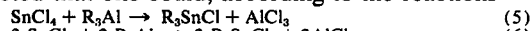
$SnCl_4 + R_3Al \rightarrow R_3SnCl + AlCl_3$ (5)
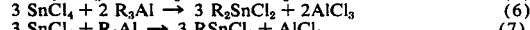
$3 SnCl_4 + 2 R_3Al \rightarrow 3 R_2SnCl_2 + 2AlCl_3$ (6)
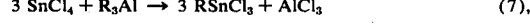
$3 SnCl_4 + R_3Al \rightarrow 3 RSnCl_3 + AlCl_3$ (7), produce the different organotin halides according to choice. In the cases represented by equations (5) and (6), this could in fact be carried out satisfactorily . . . , if the $AlCl_3$ formed could be removed from the reaction mixture by complex formation with ethers or amines . . . The reaction (7) has not yet been realized."

The surprising discovery has now been made that the aforementioned reaction (7) can in fact be carried out if one observes the features of the present invention.

The process of the present invention for the preparation of alkyl tin trichlorides by the monoalkylation of tin tetrachloride involves:

1. the use of the reagents in stoichiometric proportions, i.e. $SnCl_4$ is reacted with such an amount of alkyl aluminum compound (such as an aluminum trialkyl or alkyl aluminum halide) as will provide only one alkyl group per tin atom;
2. at least the aluminum alkyl compound is reacted in the form of its donor complex with an ether or a tertiary amine;
3. the aluminum alkyl donor complex is reacted by addition to the tin tetrachloride; and
4. the reaction is carried out at a temperature from 20° to 70° C., preferably between 40° and 70° C.

If these four conditions are all observed, the yields of alkyl tin trichloride are at least 65 percent. Indeed, using certain reagents (e.g. trioctyl aluminum butyl etherate complex) under certain conditions (e.g. with the tin tetrachloride reagent also present as a butyl etherate complex), minimum yields of 95 percent of alkyl tin trichloride can be prepared. On the other hand, failure to observe one or more of the aforementioned criteria results in significant decreases in the product yield.

For the process of the invention, the donor complexes of alkyl aluminum compounds with ethers such as diethyl ether, di-n-butyl ether, tetrahydrofuran, dioxane, anisole, etc., or with amines such as triethylamine, pyridine, or dimethyl aniline, etc. are suitable. Several donor complexes, for example those with tetrahydrofuran or pyridine, alkylate the $SnCl_4$ to a product mixture $R_nSnCl_{4-n}$, where $n = 1 - 4$, but in which, nevertheless, the alkyl tin trichloride is the principal product.

The di-n-butyl ether complex, either with trialkyl aluminum or with alkyl auminum halides, has proved particularly advantageous according to the process of the present invention. Alkyl tin trichlorides are obtained in an amount of about 85 – 95 weight percent. This can be increased to 97 to 99 percent if the $SnCl_4$ is also employed as an etherate complex.

The process according to the present invention for the preparation of alkyl tin trichlorides is explained in more detail below.

First, the alkyl aluminum compound is mixed with the desired donor in a known fashion in a suitable apparatus under a protective atmosphere. Then the alkyl aluminum-complex compound so formed is combined, also under a protective atmosphere, with $SnCl_4$ or, optionally, with a mixture of $SnCl_4$ and di-n-butyl ether in such a mol ratio that one alkyl group is present for each Sn atom. This process is suitably carried out by introducing the $SnCl_4$ into the reaction apparatus and allowing the alkyl aluminum complex compound to flow thereinto, with good mixing. Since this is an exothermic process, good cooling is employed to maintain a low temperature during the reaction. As mentioned above, the reaction is carried out at temperatures between 20° and 70° C., preferably between 40° and 70° C., and suitably at about 40° C. At higher temperatures, a larger portion of by-products is formed. Additionally, there is a danger of decomposition of the donor complex of the aluminum compound.

At the end of the reaction and post-reaction, the reaction mixture is suitably diluted with an appropriate solvent and poured into ice water. A suitable solvent is di-n-butyl ether, for example. (Dilution with di-n-butyl ether can be omitted if this material is added at the beginning to the $SnCl_4$.) The subsequent addition of di-n-butyl ether has no further influence on the product composition and is solely to permit better working up of the reaction product. Namely, if the addition of a solvent such as di-n-butyl ether is omitted, then the aqueous phase must be extracted several times with, for example, di-n-butyl ether, particularly in the preparation of $RSnCl_3$ having a short-chain R group. After phase separation and distillative removal of the di-n-butyl ether, alkyl tin trichloride is obtained in admixture with varying small amounts of higher akylated tin chlorides or tetraalkyl tin.

After phase separation, the di-n-butyl ether is distilled from the ether phase under reduced pressure and the $C_8H_{17}SnCl_3$ is obtained as a brightly-colored to darkbrown liquid. The yield is 322 g (90 percent, calculated on the Sn introduced).

Gas chromatographic analysis with a sample reacted with $C_2H_5MgCl$ gave a content of $C_8H_{17}SnCl_3$ of 93 weight percent.

EXAMPLE 2

Using the apparatus described in Example 1, 260 g (2 mols) of di-n-butyl ether are added with stirring to 260.5 g (1 mol) of $SnCl_4$. The temperature rises to about 60° C. Since this reaction mixture solidifies between 40° C. and 50° C., further reaction with $(C_8H_{17})_3Al.(C_4H_9)_2O$ occurs at 50° C. and proceeds generally as in Example 1. The yield is 90 percent; the gas chromatographically determined content of $C_8H_{17}SnCl_3$ is 97 percent.

EXAMPLE 3

$SnCl_4$ is reacted with $(C_8H_{17})_3Al.(C_4H_9)_2O$ as in Example 1. However, there is no further addition of di-n-butyl ether. After hydrolysis of the reaction mixture, the aqueous phase is extracted two or three times with 70 – 100 ml portions of di-n-butyl ether and the reaction product is isolated as in Example 1.

A yield of 90 percent is obtained. The gas chromatograhically-determined content of $C_8H_{17}SnCl_3$ is 97 percent.

| Example No. | Al-alkyl-Compound | Donor | Temperature (° C.) | Yield (%) | $RSnCl_3$ (Weight Percent)* |
|---|---|---|---|---|---|
| 4  | $(C_8H_{17})_3Al$ | $(C_4H_9)_2O$ | 40 | 90 | 95 |
| 5  | $(C_8H_{17})_3Al$ | $(C_4H_9)_2O$ | 70 | 85 | 91 |
| 6  | $(C_8H_{17})_3Al$ | $(C_2H_5)_2O$ | 30 | 80 | 87 |
| 7  | $(C_8H_{17})_3Al$ | Dioxane | 40 | 80 | 84 |
| 8  | $(C_8H_{17})_3Al$ | THF | 30 | 80 | 72 |
| 9  | $(C_8H_{17})_3Al$ | Anisole | 30 | 80 | 91 |
| 10 | $C_8H_{17}AlCl_2$ | $(C_4H_9)_2O$ | 40 | 90 | 99 |
| 11 | $(C_8H_{17})_3Al$ | Pyridine | 30 | 60 | 77 |
| 12 | $(C_8H_{17})_3Al$ | $(C_2H_5)_3N$ | 30 | 60 | 89 |
| 13 | $(C_8H_{17})_3Al$ | DMA | 30 | 60 | 79 |
| 14 | $(C_{18}H_{37})_3Al$ | $(C_4H_9)_2O$ | 50 | 80 | 85 |
| 15 | $(C_4H_9)_3Al$ | $(C_4H_9)_2O$ | 40 | 85 | 87 |
| 16 | $(C_4H_9)_3Al$ | THF | 30 | 80 | 68 |
| 17 | $(C_4H_9)_3Al$ | $(C_2H_5)_2O$ | 30 | 70 | 65 |
| 18 | $(C_4H_9)_3Al$ | Anisole | 40 | 80 | 73 |

THF=Tetrahydrofuran
DMA=Dimethyl aniline
*=Area percent in the gas chromatogram

A better understanding of the present invention and of its many advantages will be had by referring to the following specific examples, given by way of illustration.

EXAMPLE 1

171 g of $(C_8H_{17})_3Al.(C_4H_9)_2O$ (corresponding to 0.33 mol of tri-n-octyl aluminum) are added with stirring and cooling at 40° C. to 260.5 g (1 mol) of $SnCl_4$ in a one liter three-necked flask equipped with a stirrer, Claisen attachment, thermometer, reflux condenser, and dropping funnel. After addition is complete, the mixture is stirred for an additional 30 minutes at 40° C. and then, 260 g (2 mols) of di-n-butyl ether are added, again with stirring and cooling to 40° – 50° C. After conclusion of this addition, the mixture is stirred for a further 15 minutes without heating or cooling and is poured with cooling into 200 ml of ice water. In this process, the temperature is kept at 50° – 70° C. at most.

The following Comparison Examples illustrate the effect of deviating from the four criteria which, according to the invention, are critical to obtaining a high yield of final product.

COMPARISON EXAMPLE 1

The process of Example 1 was carried out with the difference that the $(C_8H_{17})_3Al$ was not added as an etherate complex. The reaction product had the following composition.

$RSnCl_3$ = 10 weight percent
$R_2SnCl_2$ = 5 weight percent
(R = $C_8H_{17}$-)
$R_3SnCl$ = 83 weight percent
$R_4Sn$ = 2 weight percent
Total yield calculated on the tin employed: 88 percent ($RSnCl_3 + R_2SnCl_2 + R_3SnCl + R_4Sn$).

COMPARISON EXAMPLE 2

The process was carried out as in Example 1 with the difference that the $SnCl_4$ was added to the alkyl aluminum donor complex. The reaction product had the following composition:

$RSnCl_3$ = 73 weight percent
$R_2SnCl_2$ = 8 weight percent
($R = C_8H_{17}$-)
$R_3SnCl$ = 19 weight percent Total yield calculated on the tin employed: 95 percent ($RSnCl_3 + R_2SnCl_2 + R_3SnCl$).

COMPARISON EXAMPLE 3

Example 1 was repeated with the difference that the necessary stoichiometric ratio for the preparation of monoalkyl tin trichloride was not maintained. Products of the following composition were obtained:

| Mol Ratio of $SnCl_4$:$(C_8H_{17})_3Al \cdot (C_4H_9)_2O$ | Temperature (° C.) | Composition in Percent by Weight | | | | Total Yield* |
| --- | --- | --- | --- | --- | --- | --- |
| | | $RSnCl_3$ | $R_2SnCl_2$ | $R_3SnCl$ | $R_4Sn$ | |
| 1:0.66 | 40 | 28 | 55 | 14 | 3 | 98 |
| 1:1 | 40 | 7 | 60 | 12 | 21 | 98 |
| 1:1.33 | 40 | 2 | 37 | 13 | 48 | 99 |

*Calculated on the tin employed, i.e. percent ($RSnCl_3 + R_2SnCl_2 + R_3SnCl + R_4Sn$)

COMPARISON EXAMPLE 4

Example 1 was carried out with the exception that the reaction temperature was raised to 100° C. A product of the following composition was obtained:

$RSnCl_3$ = 75 weight percent
$R_2SnCl_2$ = 25 weight percent

Total yield based on the tin employed: 90 percent ($RSnCl_3 + R_2SnCl_2$).

What is claimed is:

1. A method for making an alkyl tin trichloride by the monoalkylation of tin tetrachloride which comprises adding an aluminum trialkyl or alkyl aluminum halide to tin tetrachloride in a stoichiometric amount for the production of monoakyl tin trichloride and at a temperature between 20° and 70° C., said aluminum trialkkyl or alkyl aluminum halide having from 4 – 18 carbon atoms in each alkyl group and being in the form of a donor complex with an ether or a tertiary amine.

2. A method as in claim 1 wherein said temperature is between 40° and 70° C.

3. A method as in claim 1 wherein said ether or tertiary amine in said donor complex is a member selected from the group consisting of diethyl ether, di-n-butyl ether, dioxane, tetrahydrofuran, anisole, triethylamine, dimethylaniline, and pyridine.

4. A method as in claim 1 wherein the yield of said alkyl tin trichloride is at least 65 percent.

5. A method as in claim 1 wherein the donor complex of trioctyl aluminum with di-n-butyl ether is reacted with tin tetrachloride.

6. A method as in claim 5 wherein the yield of said akyl tin trichloride is at least 85 percent.

7. A method as in claim 5 wherein said tin tetrachloride is reacted in the form of its di-n-butyl etherate complex.

8. A method as in claim 7 wherein the yield of said alkyl tin trichloride is at least 97 percent.

* * * * *